United States Patent
Gilboa et al.

(10) Patent No.: US 9,055,881 B2
(45) Date of Patent: Jun. 16, 2015

(54) SYSTEM AND METHOD FOR IMAGE-BASED ALIGNMENT OF AN ENDOSCOPE

(75) Inventors: Pinhas Gilboa, Haifa (IL); Danny Blecher, Ramat Gan (IL); Benny Greenberg, Hod Hasharon (IL)

(73) Assignee: Super Dimension Ltd. (IL)

( * ) Notice: Subject to any disclaimer, the term of this patent is extended or adjusted under 35 U.S.C. 154(b) by 1668 days.

(21) Appl. No.: 11/568,260

(22) PCT Filed: May 1, 2005

(86) PCT No.: PCT/IL2005/000452
§ 371 (c)(1),
(2), (4) Date: Apr. 22, 2008

(87) PCT Pub. No.: WO2005/102175
PCT Pub. Date: Nov. 3, 2005

(65) Prior Publication Data
US 2008/0262297 A1     Oct. 23, 2008

(51) Int. Cl.
  A61B 1/04  (2006.01)
  A61B 1/00  (2006.01)
  (Continued)

(52) U.S. Cl.
  CPC ............. *A61B 1/05* (2013.01); *A61B 1/00128* (2013.01); *A61B 1/00137* (2013.01); *A61B 1/0014* (2013.01); *A61B 1/00147* (2013.01); *A61B 1/0052* (2013.01); *A61B 1/012* (2013.01); *A61B 1/018* (2013.01); *A61B 1/042* (2013.01); *A61B 1/2676* (2013.01); *A61B 5/06* (2013.01);
  (Continued)

(58) Field of Classification Search
  CPC .......... A61B 1/00147; A61B 19/5244; A61B 19/5225; A61B 5/06–5/068
  USPC .................. 600/103, 109, 117, 188, 424, 921
  See application file for complete search history.

(56) References Cited

U.S. PATENT DOCUMENTS

| 1,576,781 A | 3/1926 | Phillips |
| 1,735,726 A | 11/1929 | Bornhardt |

(Continued)

FOREIGN PATENT DOCUMENTS

| CA | 964149 | 3/1975 |
| DE | 3042343 A1 | 6/1982 |

(Continued)

OTHER PUBLICATIONS

European Patent Office, Supplementary European Search Report dated Sep. 18, 2008, 4 pages.
(Continued)

*Primary Examiner* — Anhtuan T Nguyen
*Assistant Examiner* — William Chou
(74) *Attorney, Agent, or Firm* — Carter, DeLuca, Farrell & Schmidt, LLP

(57) ABSTRACT

Systems and methods for endoscopic procedures employ a first technique to ensure initial correct alignment of an endoscope (100) with a desired target (10). A reference image (51) is then acquired from an imaging arrangement associated with the endoscope. During a subsequent stage of the procedure, tracking of the endoscope position relative to the target is performed partially or entirely by image-based tracking by comparing features in real-time video image (52) produced by imaging arrangement with features in the reference image (51). The feature comparison may be performed visually by a user, or may be automated to offer more specific corrective suggestions to the user.

17 Claims, 7 Drawing Sheets

(51) Int. Cl.

| | | |
|---|---|---|
| A61B 1/05 | (2006.01) | |
| A61B 1/005 | (2006.01) | |
| A61B 1/012 | (2006.01) | |
| A61B 1/018 | (2006.01) | |
| A61B 1/267 | (2006.01) | |
| A61B 5/06 | (2006.01) | |
| A61B 5/00 | (2006.01) | |
| A61B 19/00 | (2006.01) | |

(52) U.S. Cl.
CPC ............... *A61B5/415* (2013.01); *A61B 5/418* (2013.01); *A61B 19/26* (2013.01); *A61B 2019/267* (2013.01); *A61B 2019/5291* (2013.01); *A61B 1/0005* (2013.01)

(56) References Cited

U.S. PATENT DOCUMENTS

| | | |
|---|---|---|
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,191,652 A | 6/1965 | Benson et al. |
| 3,294,083 A | 12/1966 | Alderson |
| 3,310,264 A | 3/1967 | Appleton |
| 3,367,326 A | 2/1968 | Frazier |
| 3,439,256 A | 4/1969 | Kahne et al. |
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,747,166 A | 7/1973 | Eross |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,024,997 A | 5/1977 | Kolpin |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,403,321 A | 9/1983 | Kruger |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,447,224 A | 5/1984 | DeCant, Jr. et al. |
| 4,447,462 A | 5/1984 | Tafuri et al. |
| 4,485,815 A | 12/1984 | Amplatz et al. |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,586,491 A | 5/1986 | Carpenter |
| 4,607,619 A | 8/1986 | Seike et al. |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,669,172 A | 6/1987 | Petruzzi |
| 4,673,352 A | 6/1987 | Hansen |
| 4,685,583 A | 8/1987 | Noon |
| 4,688,037 A | 8/1987 | Krieg |
| 4,701,049 A | 10/1987 | Beckman et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,787,591 A | 11/1988 | Villacorta |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,679 A | 3/1989 | Shimonaka et al. |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |

(56) References Cited

U.S. PATENT DOCUMENTS

| | | |
|---|---|---|
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,951,677 A | 8/1990 | Crowley et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 4,994,069 A | 2/1991 | Ritchart et al. |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,021,888 A | 6/1991 | Kondou et al. |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,186 A | 10/1991 | Yamamoto et al. |
| 5,059,789 A | 10/1991 | Salcudean |
| 5,078,140 A | 1/1992 | Kwoh |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,104,393 A | 4/1992 | Isner et al. |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,160,337 A | 11/1992 | Cosman |
| 5,161,536 A | 11/1992 | Vilkomerson et al. |
| 5,171,245 A | 12/1992 | Cezana |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,622 A | 7/1993 | Brossoit |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A * | 11/1993 | Mick et al. .................... 600/425 |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,301,061 A | 4/1994 | Nakada et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,320,249 A | 6/1994 | Strech |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,341,807 A | 8/1994 | Nardella |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Muller et al. |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,380,302 A | 1/1995 | Orth |
| 5,383,454 A | 1/1995 | Bucholz |
| 5,383,852 A | 1/1995 | Stevens-Wright |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,400,771 A * | 3/1995 | Pirak et al. .................... 600/109 |
| 5,402,801 A | 4/1995 | Taylor |
| 5,408,409 A | 4/1995 | Glassman et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |

(56) References Cited

U.S. PATENT DOCUMENTS

| | | |
|---|---|---|
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,474,075 A | 12/1995 | Goldberg et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,489,256 A | 2/1996 | Adair |
| 5,490,196 A | 2/1996 | Rudich et al. |
| 5,494,034 A | 2/1996 | Schlondorff et al. |
| 5,503,416 A | 4/1996 | Aoki et al. |
| 5,506,102 A | 4/1996 | McDonnell |
| 5,513,637 A | 5/1996 | Twiss et al. |
| 5,514,146 A | 5/1996 | Lam et al. |
| 5,515,160 A | 5/1996 | Schulz et al. |
| 5,515,641 A | 5/1996 | D'Alessandro |
| 5,517,990 A | 5/1996 | Kalfas et al. |
| 5,522,815 A | 6/1996 | Durgin, Jr. et al. |
| 5,531,227 A | 7/1996 | Schneider |
| 5,531,520 A | 7/1996 | Grimson et al. |
| 5,531,686 A | 7/1996 | Lundquist et al. |
| 5,535,973 A | 7/1996 | Bailey et al. |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,555,883 A | 9/1996 | Avitall |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-haim |
| 5,571,083 A | 11/1996 | Lemelson |
| 5,572,999 A | 11/1996 | Funda et al. |
| 5,573,493 A | 11/1996 | Sauer et al. |
| 5,573,533 A | 11/1996 | Strul |
| 5,575,794 A | 11/1996 | Walus et al. |
| 5,575,798 A | 11/1996 | Koutrouvelis |
| 5,577,991 A | 11/1996 | Akui et al. |
| 5,583,909 A | 12/1996 | Hanover |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,600,330 A | 2/1997 | Blood |
| 5,603,318 A | 2/1997 | Heilbrun et al. |
| 5,611,025 A | 3/1997 | Lorensen et al. |
| 5,617,462 A | 4/1997 | Spratt |
| 5,617,857 A | 4/1997 | Chader et al. |
| 5,619,261 A | 4/1997 | Anderton |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,175 A | 7/1997 | Adair |
| 5,643,268 A | 7/1997 | Vilsmeier et al. |
| 5,645,065 A | 7/1997 | Shapiro et al. |
| 5,646,524 A | 7/1997 | Gilboa |
| 5,647,361 A | 7/1997 | Damadian |
| 5,662,111 A | 9/1997 | Cosman |
| 5,664,001 A | 9/1997 | Tachibana et al. |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,696,500 A | 12/1997 | Diem |
| 5,697,377 A | 12/1997 | Wittkampf |
| 5,702,406 A | 12/1997 | Vilsmeier et al. |
| 5,711,299 A | 1/1998 | Manwaring et al. |
| 5,713,853 A | 2/1998 | Clark et al. |
| 5,713,946 A | 2/1998 | Ben-Haim |
| 5,715,822 A | 2/1998 | Watkins et al. |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,728,047 A | 3/1998 | Edoga |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,735,278 A | 4/1998 | Hoult et al. |
| 5,738,096 A | 4/1998 | Ben-Haim |
| 5,740,802 A | 4/1998 | Nafis et al. |
| 5,741,214 A | 4/1998 | Ouchi et al. |
| 5,742,394 A | 4/1998 | Hansen |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,755,725 A | 5/1998 | Druais |
| RE35,816 E | 6/1998 | Schulz |
| 5,758,667 A | 6/1998 | Slettenmark |
| 5,762,064 A | 6/1998 | Polvani |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,775,322 A | 7/1998 | Silverstein et al. |
| 5,776,064 A | 7/1998 | Kalfas et al. |
| 5,782,765 A | 7/1998 | Jonkman |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,089 A | 9/1998 | Ferre et al. |
| 5,807,252 A | 9/1998 | Hassfeld et al. |
| 5,810,008 A | 9/1998 | Dekel et al. |

(56) References Cited

U.S. PATENT DOCUMENTS

| | | |
|---|---|---|
| 5,810,728 A | 9/1998 | Kuhn |
| 5,810,735 A | 9/1998 | Halperin et al. |
| 5,820,553 A | 10/1998 | Hughes |
| 5,820,591 A | 10/1998 | Thompson et al. |
| 5,823,192 A | 10/1998 | Kalend et al. |
| 5,823,958 A | 10/1998 | Truppe |
| 5,828,725 A | 10/1998 | Levinson |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim |
| 5,842,984 A | 12/1998 | Avitall |
| 5,843,051 A | 12/1998 | Adams et al. |
| 5,843,076 A | 12/1998 | Webster, Jr. et al. |
| 5,846,183 A | 12/1998 | Chilcoat |
| 5,848,967 A | 12/1998 | Cosman |
| 5,851,183 A | 12/1998 | Bucholz |
| 5,865,726 A | 2/1999 | Katsurada et al. |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,873,822 A | 2/1999 | Ferre et al. |
| 5,879,499 A | 3/1999 | Corvi |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,157 A | 4/1999 | Day et al. |
| 5,893,885 A | 4/1999 | Webster, Jr. |
| 5,904,691 A | 5/1999 | Barnett et al. |
| 5,907,395 A | 5/1999 | Schulz et al. |
| 5,913,820 A | 6/1999 | Bladen et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,935,160 A | 8/1999 | Auricchio et al. |
| 5,938,603 A | 8/1999 | Ponzi |
| 5,938,694 A | 8/1999 | Jaraczewski et al. |
| 5,947,925 A | 9/1999 | Ashiya et al. |
| 5,947,980 A | 9/1999 | Jensen et al. |
| 5,947,981 A | 9/1999 | Cosman |
| 5,950,629 A | 9/1999 | Taylor et al. |
| 5,951,475 A | 9/1999 | Gueziec et al. |
| 5,951,571 A | 9/1999 | Audette |
| 5,954,647 A | 9/1999 | Bova et al. |
| 5,954,796 A | 9/1999 | McCarty et al. |
| 5,957,844 A | 9/1999 | Dekel et al. |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,004,269 A | 12/1999 | Crowley et al. |
| 6,006,126 A | 12/1999 | Cosman |
| 6,006,127 A | 12/1999 | Van Der Brug et al. |
| 6,013,087 A | 1/2000 | Adams et al. |
| 6,014,580 A | 1/2000 | Blume et al. |
| 6,016,439 A | 1/2000 | Acker |
| 6,019,725 A | 2/2000 | Vesely et al. |
| 6,024,695 A | 2/2000 | Taylor et al. |
| 6,035,229 A | 3/2000 | Silverstein et al. |
| 6,050,724 A | 4/2000 | Schmitz et al. |
| 6,059,718 A | 5/2000 | Taniguchi et al. |
| 6,061,588 A | 5/2000 | Thornton et al. |
| 6,063,022 A | 5/2000 | Ben-Haim |
| 6,071,288 A | 6/2000 | Carol et al. |
| 6,073,043 A | 6/2000 | Schneider |
| 6,076,008 A | 6/2000 | Bucholz |
| 6,086,529 A | 7/2000 | Arndt |
| 6,096,050 A | 8/2000 | Audette |
| 6,104,944 A | 8/2000 | Martinelli |
| 6,112,111 A | 8/2000 | Glantz |
| 6,117,070 A | 9/2000 | Akiba |
| 6,118,845 A | 9/2000 | Simon et al. |
| 6,122,538 A | 9/2000 | Sliwa, Jr. et al. |
| 6,122,541 A | 9/2000 | Cosman et al. |
| 6,131,396 A | 10/2000 | Duerr et al. |
| 6,134,003 A | 10/2000 | Tearney et al. |
| 6,139,183 A | 10/2000 | Graumann |
| 6,147,480 A | 11/2000 | Osadchy et al. |
| 6,149,592 A | 11/2000 | Yanof et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,171,303 B1 | 1/2001 | Ben-Haim et al. |
| 6,172,499 B1 | 1/2001 | Ashe |
| 6,175,756 B1 | 1/2001 | Ferre et al. |
| 6,178,345 B1 | 1/2001 | Vilsmeier et al. |
| 6,183,444 B1 | 2/2001 | Glines et al. |
| 6,188,355 B1 | 2/2001 | Gilboa |
| 6,192,280 B1 | 2/2001 | Sommer et al. |
| 6,194,639 B1 | 2/2001 | Botella et al. |
| 6,200,262 B1 | 3/2001 | Ouchi |
| 6,201,387 B1 | 3/2001 | Govari |
| 6,203,493 B1 | 3/2001 | Ben-Haim |
| 6,203,497 B1 | 3/2001 | Dekel et al. |
| 6,210,362 B1 | 4/2001 | Ponzi |
| 6,210,378 B1 | 4/2001 | Ouchi |
| 6,211,666 B1 | 4/2001 | Acker |
| 6,213,995 B1 | 4/2001 | Steen et al. |
| 6,216,027 B1 | 4/2001 | Willis et al. |
| 6,223,067 B1 | 4/2001 | Vilsmeier et al. |
| 6,226,543 B1 | 5/2001 | Gilboa et al. |
| 6,233,476 B1 | 5/2001 | Strommer et al. |
| 6,236,875 B1 | 5/2001 | Bucholz et al. |
| 6,246,231 B1 | 6/2001 | Ashe |
| 6,246,784 B1 | 6/2001 | Summers et al. |
| 6,253,770 B1 | 7/2001 | Acker et al. |
| 6,259,942 B1 | 7/2001 | Westermann et al. |
| 6,273,896 B1 | 8/2001 | Franck et al. |
| 6,285,902 B1 | 9/2001 | Kienzle, III et al. |
| 6,286,798 B1 | 9/2001 | Chun |
| 6,298,262 B1 | 10/2001 | Franck et al. |
| 6,306,097 B1 | 10/2001 | Park et al. |
| 6,314,310 B1 | 11/2001 | Ben-Haim et al. |
| 6,319,250 B1 | 11/2001 | Falwell et al. |
| 6,332,089 B1 | 12/2001 | Acker et al. |
| 6,335,617 B1 | 1/2002 | Osadchy et al. |
| 6,341,231 B1 | 1/2002 | Ferre et al. |
| 6,343,728 B1 | 2/2002 | Carbone |
| 6,345,112 B1 | 2/2002 | Summers et al. |
| 6,346,940 B1 * | 2/2002 | Fukunaga .................... 345/427 |
| 6,351,659 B1 | 2/2002 | Vilsmeier |
| 6,355,027 B1 | 3/2002 | Le et al. |
| 6,366,799 B1 | 4/2002 | Acker et al. |
| 6,368,316 B1 | 4/2002 | Jansen et al. |
| 6,373,240 B1 | 4/2002 | Govari |
| 6,381,485 B1 | 4/2002 | Hunter et al. |
| 6,381,490 B1 | 4/2002 | Ostrovsky |
| 6,422,994 B1 | 7/2002 | Kaneko et al. |
| 6,423,009 B1 | 7/2002 | Downey et al. |
| 6,424,856 B1 | 7/2002 | Vilsmeier et al. |
| 6,427,314 B1 | 8/2002 | Acker |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,443,894 B1 | 9/2002 | Sumanaweera et al. |
| 6,445,943 B1 | 9/2002 | Ferre et al. |

(56) References Cited

U.S. PATENT DOCUMENTS

| | | | |
|---|---|---|---|
| 6,447,504 B1 | 9/2002 | Ben-Haim et al. | |
| 6,453,190 B1 | 9/2002 | Acker et al. | |
| 6,468,265 B1 | 10/2002 | Evans et al. | |
| 6,470,207 B1 | 10/2002 | Simon et al. | |
| 6,474,341 B1 | 11/2002 | Hunter et al. | |
| 6,478,802 B2 | 11/2002 | Kienzle, III et al. | |
| 6,484,049 B1 | 11/2002 | Seeley et al. | |
| 6,484,118 B1 | 11/2002 | Govari | |
| 6,485,413 B1 | 11/2002 | Boppart et al. | |
| 6,490,475 B1 | 12/2002 | Seeley et al. | |
| 6,493,573 B1 | 12/2002 | Martinelli et al. | |
| 6,498,944 B1 | 12/2002 | Ben-Haim et al. | |
| 6,499,488 B1 | 12/2002 | Hunter et al. | |
| 6,503,195 B1 * | 1/2003 | Keller et al. | 600/160 |
| 6,516,046 B1 | 2/2003 | Frohlich et al. | |
| 6,527,443 B1 | 3/2003 | Vilsmeier et al. | |
| 6,547,722 B1 | 4/2003 | Higuma et al. | |
| 6,551,325 B2 | 4/2003 | Neubauer et al. | |
| 6,579,277 B1 | 6/2003 | Rabiner et al. | |
| 6,580,938 B1 | 6/2003 | Acker | |
| 6,584,174 B2 | 6/2003 | Schubert et al. | |
| 6,585,639 B1 | 7/2003 | Kotmel et al. | |
| 6,591,129 B1 | 7/2003 | Ben-Haim et al. | |
| 6,593,884 B1 | 7/2003 | Gilboa et al. | |
| 6,609,022 B2 | 8/2003 | Vilsmeier et al. | |
| 6,611,700 B1 | 8/2003 | Vilsmeier et al. | |
| 6,612,485 B2 | 9/2003 | Lackner et al. | |
| 6,618,612 B1 | 9/2003 | Acker et al. | |
| 6,626,339 B2 | 9/2003 | Gates et al. | |
| 6,628,980 B2 | 9/2003 | Atalar et al. | |
| 6,631,876 B1 | 10/2003 | Phillips | |
| 6,640,128 B2 | 10/2003 | Vilsmeier et al. | |
| 6,650,927 B1 | 11/2003 | Keidar | |
| 6,666,864 B2 | 12/2003 | Bencini et al. | |
| 6,676,659 B2 | 1/2004 | Hutchins et al. | |
| 6,690,963 B2 | 2/2004 | Ben-Haim et al. | |
| 6,694,162 B2 | 2/2004 | Hartlep | |
| 6,701,179 B1 | 3/2004 | Martinelli et al. | |
| 6,706,041 B1 | 3/2004 | Costantino | |
| 6,711,429 B1 | 3/2004 | Gilboa et al. | |
| 6,712,842 B1 | 3/2004 | Gifford, III et al. | |
| 6,751,492 B2 | 6/2004 | Ben-Haim | |
| 6,770,027 B2 | 8/2004 | Banik et al. | |
| 6,788,967 B2 | 9/2004 | Ben-Haim et al. | |
| 6,796,963 B2 | 9/2004 | Carpenter et al. | |
| 6,850,794 B2 * | 2/2005 | Shahidi | 600/427 |
| 6,887,236 B2 | 5/2005 | Gilboa | |
| 6,947,788 B2 | 9/2005 | Gilboa et al. | |
| 6,960,161 B2 | 11/2005 | Amling et al. | |
| 6,995,729 B2 | 2/2006 | Govari et al. | |
| 7,022,066 B2 | 4/2006 | Yokoi et al. | |
| 7,101,380 B2 | 9/2006 | Khachin et al. | |
| 7,182,756 B2 | 2/2007 | Saeed et al. | |
| 7,197,354 B2 | 3/2007 | Sobe | |
| 7,233,820 B2 | 6/2007 | Gilboa | |
| 7,236,567 B2 | 6/2007 | Sandkamp et al. | |
| 7,286,868 B2 | 10/2007 | Govari | |
| 7,301,332 B2 | 11/2007 | Govari et al. | |
| 7,321,228 B2 | 1/2008 | Govari | |
| 7,324,915 B2 | 1/2008 | Altmann et al. | |
| 7,343,195 B2 | 3/2008 | Strommer et al. | |
| 7,353,125 B2 | 4/2008 | Nieminen et al. | |
| 7,357,795 B2 | 4/2008 | Kaji et al. | |
| 7,366,562 B2 | 4/2008 | Dukesherer et al. | |
| 7,370,656 B2 | 5/2008 | Gleich et al. | |
| 7,373,271 B1 | 5/2008 | Schneider | |
| 7,386,339 B2 | 6/2008 | Strommer et al. | |
| 7,397,364 B2 | 7/2008 | Govari | |
| 7,399,296 B2 | 7/2008 | Poole et al. | |
| 7,497,029 B2 | 3/2009 | Plassky et al. | |
| 7,505,809 B2 | 3/2009 | Strommer et al. | |
| 7,536,218 B2 | 5/2009 | Govari et al. | |
| RE40,852 E | 7/2009 | Martinelli et al. | |
| 7,570,987 B2 | 8/2009 | Raabe et al. | |
| 7,577,474 B2 | 8/2009 | Vilsmeier | |
| 7,579,837 B2 | 8/2009 | Fath et al. | |
| 7,587,235 B2 | 9/2009 | Wist et al. | |
| 7,597,296 B2 | 10/2009 | Conway | |
| 7,599,535 B2 | 10/2009 | Kiraly et al. | |
| 7,599,810 B2 | 10/2009 | Yamazaki | |
| 7,630,753 B2 | 12/2009 | Simon et al. | |
| 7,634,122 B2 | 12/2009 | Bertram et al. | |
| 7,636,595 B2 | 12/2009 | Marquart et al. | |
| 7,641,609 B2 | 1/2010 | Ohnishi et al. | |
| 7,648,458 B2 | 1/2010 | Niwa et al. | |
| 7,652,468 B2 | 1/2010 | Kruger et al. | |
| 7,657,300 B2 | 2/2010 | Hunter et al. | |
| 7,659,912 B2 | 2/2010 | Akimoto et al. | |
| 7,660,623 B2 | 2/2010 | Hunter et al. | |
| 7,680,528 B2 | 3/2010 | Pfister et al. | |
| 7,684,849 B2 | 3/2010 | Wright et al. | |
| 7,686,767 B2 | 3/2010 | Maschke | |
| 7,688,064 B2 | 3/2010 | Shalgi et al. | |
| 7,696,899 B2 | 4/2010 | Immerz et al. | |
| 7,697,972 B2 | 4/2010 | Verard et al. | |
| 7,697,973 B2 | 4/2010 | Strommer et al. | |
| 7,697,974 B2 | 4/2010 | Jenkins et al. | |
| 7,720,517 B2 | 5/2010 | Drysen | |
| 7,722,565 B2 | 5/2010 | Wood et al. | |
| 7,725,154 B2 | 5/2010 | Beck et al. | |
| 7,725,164 B2 | 5/2010 | Suurmond et al. | |
| 7,727,269 B2 | 6/2010 | Abraham-Fuchs et al. | |
| 7,729,742 B2 | 6/2010 | Govari | |
| 7,744,605 B2 | 6/2010 | Vilsmeier et al. | |
| 7,747,307 B2 | 6/2010 | Wright et al. | |
| 7,751,865 B2 | 7/2010 | Jascob et al. | |
| 8,083,432 B2 | 12/2011 | Limpert | |
| 8,317,149 B2 | 11/2012 | Greenburg et al. | |
| 8,663,088 B2 | 3/2014 | Greenburg et al. | |
| 2001/0004676 A1 | 6/2001 | Ouchi | |
| 2001/0007918 A1 | 7/2001 | Vilsmeier et al. | |
| 2001/0007925 A1 | 7/2001 | Ritchart et al. | |
| 2001/0031919 A1 | 10/2001 | Strommer et al. | |
| 2001/0034530 A1 | 10/2001 | Malackowski et al. | |
| 2001/0036245 A1 | 11/2001 | Kienzle et al. | |
| 2001/0037064 A1 * | 11/2001 | Shahidi | 600/429 |
| 2002/0026097 A1 | 2/2002 | Akiba | |
| 2002/0035864 A1 * | 3/2002 | Paltieli et al. | 73/1.01 |
| 2002/0067408 A1 | 6/2002 | Adair et al. | |
| 2002/0077544 A1 * | 6/2002 | Shahidi | 600/424 |
| 2002/0087100 A1 | 7/2002 | Onuki et al. | |
| 2002/0095081 A1 | 7/2002 | Vilsmeier | |
| 2002/0128565 A1 | 9/2002 | Rudy | |
| 2002/0137014 A1 | 9/2002 | Anderson et al. | |
| 2002/0162555 A1 | 11/2002 | West et al. | |
| 2002/0165503 A1 | 11/2002 | Morris et al. | |
| 2002/0173689 A1 | 11/2002 | Kaplan | |
| 2002/0193686 A1 | 12/2002 | Gilboa | |
| 2003/0018251 A1 | 1/2003 | Solomon | |
| 2003/0028096 A1 | 2/2003 | Niwa et al. | |
| 2003/0040657 A1 | 2/2003 | Yamaya et al. | |
| 2003/0069474 A1 * | 4/2003 | Couvillon, Jr. | 600/152 |
| 2003/0074011 A1 | 4/2003 | Gilboa et al. | |
| 2003/0086599 A1 | 5/2003 | Armato et al. | |
| 2003/0114742 A1 | 6/2003 | Lewkowicz et al. | |
| 2003/0135119 A1 * | 7/2003 | Lee et al. | 600/461 |
| 2003/0142753 A1 | 7/2003 | Gunday | |
| 2003/0160721 A1 | 8/2003 | Gilboa et al. | |
| 2003/0171653 A1 | 9/2003 | Yokoi et al. | |
| 2003/0227547 A1 | 12/2003 | Iddan | |
| 2004/0015049 A1 | 1/2004 | Zaar | |
| 2004/0024309 A1 | 2/2004 | Ferre et al. | |
| 2004/0086161 A1 | 5/2004 | Sivaramakrishna et al. | |
| 2004/0097804 A1 | 5/2004 | Sobe | |
| 2004/0138548 A1 | 7/2004 | Strommer et al. | |
| 2004/0169509 A1 | 9/2004 | Czipott et al. | |
| 2004/0249267 A1 | 12/2004 | Gilboa | |
| 2004/0260201 A1 | 12/2004 | Mueller | |
| 2005/0011786 A1 | 1/2005 | Wood et al. | |
| 2005/0033149 A1 | 2/2005 | Strommer et al. | |
| 2005/0054895 A1 * | 3/2005 | Hoeg et al. | 600/117 |
| 2005/0059890 A1 | 3/2005 | Deal et al. | |
| 2005/0080342 A1 | 4/2005 | Gilreath et al. | |
| 2005/0085715 A1 | 4/2005 | Dukesherer et al. | |

(56) References Cited

U.S. PATENT DOCUMENTS

| | | | |
|---|---|---|---|
| 2005/0085718 A1* | 4/2005 | Shahidi | 600/424 |
| 2005/0090818 A1 | 4/2005 | Pike et al. | |
| 2005/0107688 A1 | 5/2005 | Strommer | |
| 2005/0119527 A1 | 6/2005 | Banik et al. | |
| 2005/0182292 A1 | 8/2005 | Suzuki | |
| 2005/0182295 A1 | 8/2005 | Soper et al. | |
| 2005/0197566 A1 | 9/2005 | Strommer et al. | |
| 2005/0229934 A1 | 10/2005 | Willeford | |
| 2006/0015126 A1 | 1/2006 | Sher | |
| 2006/0058647 A1 | 3/2006 | Strommer et al. | |
| 2006/0064006 A1 | 3/2006 | Strommer et al. | |
| 2006/0069313 A1 | 3/2006 | Couvillon et al. | |
| 2006/0149134 A1 | 7/2006 | Soper et al. | |
| 2006/0184016 A1 | 8/2006 | Glossop | |
| 2007/0083107 A1* | 4/2007 | Ferre et al. | 600/424 |
| 2007/0163597 A1 | 7/2007 | Mikkaichi et al. | |
| 2007/0167714 A1 | 7/2007 | Kiraly et al. | |
| 2007/0167738 A1 | 7/2007 | Timinger et al. | |
| 2007/0167743 A1 | 7/2007 | Honda et al. | |
| 2007/0167804 A1* | 7/2007 | Park et al. | 600/459 |
| 2007/0167806 A1 | 7/2007 | Wood et al. | |
| 2007/0225553 A1* | 9/2007 | Shahidi | 600/103 |
| 2007/0225559 A1 | 9/2007 | Clerc et al. | |
| 2007/0265639 A1 | 11/2007 | Danek et al. | |
| 2007/0276180 A1 | 11/2007 | Greenburg et al. | |
| 2007/0287901 A1 | 12/2007 | Strommer et al. | |
| 2007/0293721 A1 | 12/2007 | Gilboa | |
| 2008/0086051 A1 | 4/2008 | Voegele | |
| 2008/0097154 A1* | 4/2008 | Makower et al. | 600/114 |
| 2008/0097187 A1 | 4/2008 | Gielen et al. | |
| 2008/0118135 A1 | 5/2008 | Averbuch et al. | |
| 2008/0125760 A1 | 5/2008 | Gilboa | |
| 2008/0132757 A1 | 6/2008 | Tgavalekos | |
| 2008/0132909 A1 | 6/2008 | Jascob et al. | |
| 2008/0132911 A1 | 6/2008 | Sobe | |
| 2008/0139886 A1 | 6/2008 | Tatsuyama | |
| 2008/0139915 A1 | 6/2008 | Dolan et al. | |
| 2008/0144909 A1 | 6/2008 | Wiemker et al. | |
| 2008/0147000 A1 | 6/2008 | Seibel et al. | |
| 2008/0154172 A1 | 6/2008 | Mauch | |
| 2008/0157755 A1 | 7/2008 | Kruger et al. | |
| 2008/0161682 A1 | 7/2008 | Kendrick et al. | |
| 2008/0162074 A1 | 7/2008 | Schneider | |
| 2008/0183071 A1 | 7/2008 | Strommer et al. | |
| 2008/0188749 A1 | 8/2008 | Rasche et al. | |
| 2009/0182224 A1 | 7/2009 | Shmarak et al. | |
| 2009/0234223 A1 | 9/2009 | Onoda et al. | |
| 2009/0318797 A1 | 12/2009 | Hadani | |
| 2010/0016757 A1 | 1/2010 | Greenburg et al. | |
| 2013/0158346 A1* | 6/2013 | Soper et al. | 600/104 |

FOREIGN PATENT DOCUMENTS

| | | |
|---|---|---|
| DE | 3508730 A1 | 9/1986 |
| DE | 3520782 A1 | 12/1986 |
| DE | 3717871 A1 | 12/1988 |
| DE | 3831278 A1 | 3/1989 |
| DE | 3838011 A1 | 7/1989 |
| DE | 4213426 A1 | 10/1992 |
| DE | 4225112 C1 | 12/1993 |
| DE | 4233978 C1 | 4/1994 |
| DE | 19610984 A1 | 9/1997 |
| DE | 19715202 A1 | 10/1998 |
| DE | 19751761 A1 | 10/1998 |
| DE | 19832296 A1 | 2/1999 |
| DE | 19747427 A1 | 5/1999 |
| DE | 10085137 T1 | 11/2002 |
| EP | 0062941 A1 | 10/1982 |
| EP | 0119660 A1 | 9/1984 |
| EP | 0155857 A2 | 9/1985 |
| EP | 0319844 A1 | 6/1989 |
| EP | 0326768 A2 | 8/1989 |
| EP | 0350996 A1 | 1/1990 |
| EP | 0419729 A1 | 4/1991 |
| EP | 0427358 A1 | 5/1991 |
| EP | 0456103 A2 | 11/1991 |
| EP | 0581704 A1 | 2/1994 |
| EP | 0600610 A2 | 6/1994 |
| EP | 0651968 A1 | 5/1995 |
| EP | 0655138 A1 | 5/1995 |
| EP | 0796633 A1 | 9/1997 |
| EP | 0857461 A2 | 8/1998 |
| EP | 0894473 A2 | 2/1999 |
| EP | 0908146 A2 | 4/1999 |
| EP | 0930046 A2 | 7/1999 |
| EP | 1078644 A1 | 2/2001 |
| EP | 1255113 A1 | 11/2002 |
| EP | 1543765 A1 | 6/2005 |
| EP | 1667749 A2 | 6/2006 |
| EP | 2096523 A1 | 9/2009 |
| FR | 2417970 A1 | 9/1979 |
| FR | 2618211 A1 | 1/1989 |
| GB | 2094590 A | 9/1982 |
| GB | 2164856 A | 4/1986 |
| JP | 63-240851 A | 10/1988 |
| JP | 03-267054 A | 11/1991 |
| JP | 06-125869 A | 5/1994 |
| JP | 06194639 A | 7/1994 |
| JP | 07-043619 A | 2/1995 |
| JP | 09-253038 A | 9/1997 |
| JP | 10-197807 A | 7/1998 |
| JP | 2000-075218 A | 3/2000 |
| JP | 2000-279379 A | 10/2000 |
| JP | 2001-231743 A | 8/2001 |
| JP | 2001-275942 A | 10/2001 |
| WO | 88/09151 A1 | 12/1988 |
| WO | 89/05123 A1 | 6/1989 |
| WO | 90/05494 A1 | 5/1990 |
| WO | 91/03982 A1 | 4/1991 |
| WO | 91/04711 A1 | 4/1991 |
| WO | 91/07726 A1 | 5/1991 |
| WO | 92/03090 A1 | 3/1992 |
| WO | 92/06645 A1 | 4/1992 |
| WO | 94/04938 A1 | 3/1994 |
| WO | 94/23647 A1 | 10/1994 |
| WO | 94/24933 A1 | 11/1994 |
| WO | 95/07055 A1 | 3/1995 |
| WO | 96/11624 A2 | 4/1996 |
| WO | 96/32059 A1 | 10/1996 |
| WO | 97/29682 A1 | 8/1997 |
| WO | 97/29684 A1 | 8/1997 |
| WO | 97/36192 A1 | 10/1997 |
| WO | 97/49453 A1 | 12/1997 |
| WO | 98/08554 A1 | 3/1998 |
| WO | 98/38908 A1 | 9/1998 |
| WO | 99/15097 A2 | 4/1999 |
| WO | 99/21498 A1 | 5/1999 |
| WO | 99/23956 A1 | 5/1999 |
| WO | 99/26549 A1 | 6/1999 |
| WO | 99/27839 A2 | 6/1999 |
| WO | 99/29253 A1 | 6/1999 |
| WO | 99/33406 A1 | 7/1999 |
| WO | 99/37208 A1 | 7/1999 |
| WO | 99/38449 A1 | 8/1999 |
| WO | 99/52094 A1 | 10/1999 |
| WO | 99/60939 A1 | 12/1999 |
| WO | 00/06701 A1 | 2/2000 |
| WO | 00/14056 A1 | 3/2000 |
| WO | 00/16684 A1 | 3/2000 |
| WO | 00/35531 A1 | 6/2000 |
| WO | 01/19235 A1 | 3/2001 |
| WO | 01/30437 A1 | 5/2001 |
| WO | 01/67035 A1 | 9/2001 |
| WO | 01/87136 A2 | 11/2001 |
| WO | 01/87398 A1 | 11/2001 |
| WO | 01/91842 A1 | 12/2001 |
| WO | 02/24054 A2 | 3/2002 |
| WO | 02/064011 A2 | 8/2002 |
| WO | 02/070047 A1 | 9/2002 |
| WO | 03/086498 A2 | 10/2003 |
| WO | 2004/023986 A1 | 3/2004 |
| WO | 2005025635 A2 | 3/2005 |

(56) References Cited

FOREIGN PATENT DOCUMENTS

| WO | 2005074380 A2 | 8/2005 |
|---|---|---|
| WO | 2006/116597 A2 | 11/2006 |
| WO | 2007109418 A2 | 9/2007 |

OTHER PUBLICATIONS

United States Patent and Trademark Office, Final Office Action mailed May 1, 2012 in U.S. Appl. No. 12/476,976, 6 pages.
European Patent Office, Decision to Grant dated Apr. 13, 2012 in European Patent Application No. 10191689, 1 page.
United States Patent and Trademark Office, Office Action mailed Feb. 22, 2012 in U.S. Appl. No. 12/233,933, 10 pages.
European Patent Office, Extended European Search Report dated Feb. 20, 2012 in European Patent Application No. 06701745, 9 pages.
United States Patent and Trademark Office, Final Office Action mailed Dec. 19, 2011 in U.S. Appl. No. 10/571,793, 8 pages.
European Patent Office, Extended European Search Report dated Nov. 22, 2011 in European Patent Application No. 11182823, 5 pages.
European Patent Office, Extended European Search Report dated Nov. 21, 2011 in European Patent Application No. 11182823, 5 pages.
United States Patent and Trademark Office, Office Action mailed Nov. 18, 2011 in U.S. Appl. No. 12/476,976, 8 pages.
Wipo, U.S. International Search Authority, International Search Report and Written Opinion mailed Oct. 7, 2011 in International Patent Application No. PCT/US2011/040579, 8 pages.
European Patent Office, Extended European Search Report dated Sep. 6, 2011 in European Patent Application No. 03719056, 6 pages.
European Patent Office, Extended European Search Report dated Sep. 6, 2011 in European Patent Application No. 11174666, 6 pages.
Japanese Patent Office, Official Action dated Aug. 23, 2011 in Japanese Patent Application No. 2007-552806, 7 pages.
Japanese Patent Office, Examiner's Report mailed Aug. 19, 2011 in Japanese Patent Application No. JP2007-552806, 7 pages.
Wipo, U.S. International Preliminary Examining Authority, International Preliminary Report on Patentability mailed Jun. 30, 2011 in International Patent Application No. PCT/US2009/069073, 6 pages.
United States Patent and Trademark Office, Office Action mailed May 24, 2011 in U.S. Appl. No. 10/571,793, 8 pages.
United States Patent and Trademark Office, Office Action mailed Mar. 31, 2011 in U.S. Appl. No. 12/643,917, 10 pages.
European Patent Office, Extended European Search Report dated Mar. 8, 2011 in European Patent Application No. 10191689, 4 pages.
United States Patent and Trademark Office, Office Action mailed Dec. 23, 2010 in U.S. Appl. No. 10/571,793, 11 pages.
European Patent Office, Supplementary European Search Report dated Nov. 15, 2010 in European Patent Application No. EP10159373.9, 12 pages.
United States Patent and Trademark Office, Office Action mailed Oct. 4. 2010 in U.S. Appl. No. 12/271,175, 11 pages.
European Patent Office, Examination Report dated Sep. 11, 2010 in European Patent Application No. 3719056, 4 pages.
United States Patent and Trademark Office, Final Office Action mailed Jun. 23, 2010 in U.S. Appl. No. 10/571,793, 10 pages.
WIPO, U.S. International Search Authority, International Search Report and Written Opinion mailed Apr. 23, 2010 in International Patent Application No. PCT/US2009/069073, 8 pages.
WIPO, U.S. International Preliminary Examining Authority, International Preliminary Report on Patentability mailed Apr. 8, 2010 in International Patent Application No. PCT/IB2008/002543, 7 pages.
European Patent Office, Examination Report dated Mar. 30, 2010 in European Patent Application No. EP05737664.2, 5 pages.
Japanese Patent Office, Official Action dated Mar. 12, 2010 in Japanese Patent Application No. 2006-526007, 5 pages.
European Patent Office, Extended European Search Report dated Dec. 1, 2009 in European Patent Application No. 09157586, 7 pages.
United States Patent and Trademark Office, Office Action mailed Nov. 27, 2009 in U.S. Appl. No. 10/571,793, 11 pages.

WIPO, U.S. International Search Authority, International Search Report and Written Opinion mailed Nov. 12, 2009 in International Patent Application No. PCT/IL2009/000697, 9 pages.
WIPO, U.S. International Search Authority, International Search Report and Written Opinion mailed Sep. 22, 2009 in International Patent Application No. PCT/IL2009/000553, 7 pages.
WIPO, U.S. International Preliminary Examining Authority, International Preliminary Report on Patentability mailed Jul. 28, 2009 in International Patent Application No. PCT/IL2005/000159, 6 pages.
European Patent Office, Examination Report dated Jul. 14, 2009 in European Patent Application No. 03719056, 6 pages.
United States Patent and Trademark Office, Office Action mailed Jun. 24, 2009 in U.S. Appl. No. 10/571,695, 11 pages.
WIPO, U.S. International Preliminary Examining Authority, International Preliminary Report on Patentability mailed Mar. 30, 2009 in International Patent Application No. PCT/IL2006/000113, 6 pages.
WIPO, U.S. International Search Authority, International Search Report and Written Opinion mailed Mar. 16, 2009 in International Patent Application No. PCT/IB2008/002543, 9 pages.
United States Patent and Trademark Office, Final Office Action mailed Mar. 12, 2009 in U.S. Appl. No. 10/597,747, 7 pages.
European Patent Office, Supplementary European Search Report dated Feb. 27, 2009 in European Patent Application No. 03719056, 6 pages.
European Patent Office, Decision to Grant dated Feb. 20, 2009 in European Patent Application No. 04770514, 24 pages.
WIPO, U.S. International Search Authority, International Search Report and Written Opinion mailed Dec. 15, 2008 in International Patent Application No. PCT/IL2006/000113, 6 pages.
Japanese Patent Office, Official Action dated Dec. 12, 2008 in Japanese Patent Application No. 2008-583508, 9 pages.
European Patent Office, Supplementary European Search Report dated Oct. 7, 2008 in European Patent Application No. 04770514, 4 pages.
United States Patent and Trademark Office, Office Action mailed Sep. 11, 2008 in U.S. Appl. No. 10/597,747, 9 pages.
WIPO, U.S. International Search Authority, International Search Report and Written Opinion mailed Jul. 11, 2008 in International Patent Application No. PCT-IL2005/000159, 12 pages.
WIPO, U.S. International Preliminary Examining Authority, International Preliminary Report on Patentability mailed Oct. 9, 2007 in International Patent Application No. PCT/IL2004/000843, 4 pages.
WIPO, U.S. International Search Authority, International Search Report and Written Opinion mailed Sep. 24, 2007 in International Patent Application No. PCT/IL2004/000843, 4 pages.
WIPO, U.S. International Search Authority, International Search Report and Written Opinion mailed Jul. 11, 2007 in International Patent Application No. PCT/IL2005/000159, 6 pages.
United States Patent and Trademark Office, Notice of Allowance mailed Oct. 6, 2006 in U.S. Appl. No. 10/491,099, 7 pages.
China Patent and Trademark Office, Office Action dated Jun. 19, 2006 in Chinese Patent Application No. 038135485, 5 pages.
United States Patent and Trademark Office, Office Action mailed Dec. 30, 2005 in U.S. Appl. No. 10/491,099, 15 pages.
United States Patent and Trademark Office, Office Action mailed Apr. 22, 2005 in U.S. Appl. No. 10/491,099, 5 pages.
United States Patent and Trademark Office, Notice of Allowance mailed Jan. 3, 2005 in U.S. Appl. No. 10/137,415, 9 pages.
Shmarak, I. et al., U.S. Appl. No. 10/986,567, filed Nov. 2004 (abandoned, unpublished), 84 pages.
United States Patent and Trademark Office, Office Action mailed Jul. 1, 2004 in U.S. Appl. No. 10/10,137,415, 14 pages.
WIPO, U.S. International Preliminary Examining Authority, International Preliminary Report on Patentability mailed Jan. 24, 2004 in International Patent Application No. PCT/IL2003/000323, 3 pages.
WIPO, U.S. International Search Authority, International Search Report mailed Dec. 8, 2003 in International Patent Application No. PCT/IL2003/000323, 1 page.
Stenoien, D.L. et al., "Ligand-Mediated Assembly and Real-Time Cellular Dynamics of Estrogen Receptor .alpha.—Coactivator Complexes in Living Cells," Molecular and Cellular Biology, Jul. 2001, pp. 4404-4412, 9 pages.

(56) References Cited

OTHER PUBLICATIONS

McKenna, N.J. et al., "Nuclear Receptor Coregulators: Cellular and Molecular Biology," Endocrine Reviews 20(3): 321-344, Jun. 1, 1999, 24 pages.

Ding, X.F. et al., "Nuclear Receptor-Binding Sites of Coactivators Glucocorticoid Receptor Interacting Protein 1 (GRIP1) and Steroid Receptor Coactivator 1 (SRC-1): Multiple Motifs with Different Binding Specificities," Molecular Endocrinology 12:302-313, Feb. 1, 1998 (9 pages).

* cited by examiner

SYSTEM AND METHOD FOR IMAGE-BASED ALIGNMENT OF AN ENDOSCOPE

FIELD AND BACKGROUND OF THE INVENTION

The present invention relates to endoscopy techniques and, in particular, it concerns a system and method for image-based alignment of an endoscope during at least part of an endoscopic procedure.

The present invention will be exemplified in the context of a system as described in the co-assigned PCT application published as WO 03/086498 entitled "Endoscope Structure and Techniques for Navigation in Branched Structure" to Gilboa, which is hereby incorporated by reference in its entirety. The aforementioned patent application discloses a method and apparatus in which a thin locatable guide, enveloped by a sheath, is used to navigate a bronchoscopic tool to a target location within the lung, aimed in particular to deliver treatments to the lung periphery beyond the bronchoscope's own reach. The coordinates of the target are predetermined based upon three-dimensional CT data. A location sensor is incorporated at the locatable guide's tip. The enveloped guide is inserted into the lung via the working channel of a bronchoscope. First, the bronchoscope's tip is directed to the furthest reachable location in the direction of the target. Next, the guide is advanced beyond the tip of the bronchoscope towards the designated target, based on the combination of the CT data and the position of the guide's tip as measured in body coordinates. When the guide's tip at the target, the guide is withdrawn, freeing the enveloping sheath for insertion a bronchoscopic tool. In order to prevent the distal end portion of the sheath from sliding away from the target, the sheath is locked to the bronchoscope's body and the bronchoscope itself is held steadily to prevent it from slipping further into the lungs or outwards. Because the airways in the periphery of the lung are narrow, approximately in the same dimensions as the sheath, sideways movements are extremely limited.

The above system may also be used to navigate the tip of the bronchoscope to a target located inside the main bronchus and not only to targets in the periphery of the lungs. Although for such centrally-located target the physician has direct visualization of the scene in front of the bronchoscope, it is not always sufficient for visually identifying the designated targets, since many of these targets are hidden in the tissue outside the airways. Hence, it is a benefit to combine the CT data into the navigational aids also for targets inside the main bronchus, where the bronchoscope can reach and direct vision exists, but yet the target itself is hidden.

When using the navigation system for navigating the tip of the bronchoscope itself, many of the mechanical features of the locatable guide described in WO 03/086498 are not needed. Specifically, the steerability of the guide is not needed, and the enveloping sheath is also not needed. However the principle of using a separate locatable guide having a location sensor at its tip and being inserted into the working channel of a regular bronchoscope actually changes the bronchoscope from a non-locatable bronchoscope to a locatable bronchoscope, thereby offering major advantages as will become clear.

As in the prior art apparatus, the locatable guide can be inserted into and withdrawn from the bronchoscope's working channel as needed. Unlike the periphery of the lung, the central airways are much wider than the bronchoscope. As a consequence, when the tip of the bronchoscope is on target, it can move sideways in addition to sliding in and out. Therefore stabilizing the bronchoscope's tip during treatment is a three dimensional task, involving the operation of the steering ability of the bronchoscope. An example for the importance for maintaining the location of the bronchoscope's tip at the designated target during the insertion of the bronchoscopic tool is the use of the Transbronchial Histology Needle, by which a needle is guided towards a target such as a lymph node which neighbors the main bronchus from the outside and thus is invisible to the bronchoscope image but its coordinates are known from the CT data. Any mistake in directing the needle may result not only in failure of the procedure, but worse, in causing damage to vital organs such as the aorta or other major blood vessels.

In principle, the same methods as presented in WO 03/086498 may be used in the context of the major airways. Specifically, by using the location of the tip of the bronchoscope as measured by the location measurement sensor, a directing display is produced corresponding to a simulation or schematic diagram of the view from the distal tip of the guide, which is based on the relative location of the target versus the position of the tip of the guide in six degrees of freedom. In the central airways, this view is supplemented by the direct video image from the bronchoscope imaging arrangement. Based on these two displays, the physician brings the tip of the bronchoscope to the target. When the tip of the bronchoscope is correctly aligned with and adjacent to the target (FIG. 7), the guide with the location sensor is withdrawn (as shown in FIG. 8), thereby freeing the bronchoscope's working channel for insertion a bronchoscopic tool FIG. 9a). Once the locatable guide is released, the directing display can no longer function for directing the tip to target. Instead, the physician has to hold the bronchoscope as steadily as possible during withdrawal of the guide and the insertion of the tool. If the bronchoscope slips from the target location (for example, as shown in FIG. 9b), the physician may notice the chance of position in the video image, but has no effective tool available to help him return the tip of the bronchoscope reliably to the desired target (other than reinserting the guide and repeating the navigation process).

Hence, it would be of benefit to have a method and corresponding system for confirming correct alignment of the tip of an endoscope after removal of a locatable guide used to achieve initial alignment, particularly for procedures involving a target which is obscured from view.

SUMMARY OF THE INVENTION

The present invention is a system and method for image-based alignment of an endoscope.

According to the teachings of the present invention there is provided, a method for confirming correct alignment of a distal end of an endoscope including an imaging arrangement during an endoscopic procedure, the method comprising: (a) positioning the distal end of the endoscope adjacent to a target location and capturing a reference image using the imaging arrangement; (b) sensing a real-time video image using the imaging arrangement; and (c) comparing features of the real-time video image with the reference image to confirm correct alignment of the endoscope.

According to a further feature of the present invention, the step of positioning employs a target location identified in three-dimensional image data of a region of a body to be treated.

According to a further feature of the present invention, the three-dimensional image data is derived from an imaging technique selected from: computerized tomography; magnetic resonance imaging; positron emission tomography; and ultrasound.

According to a further feature of the present invention, the step of positioning employs a position sensor associated with the distal end of the endoscope, the position sensor being part of a position measuring system.

According to a further feature of the present invention, the step of positioning is performed by comparing the position of the distal end of the endoscope as measured by the position measuring system and the target location as identified in the image data.

According to a further feature of the present invention, the position sensor is part of an elongated element deployed within a working channel of the endoscope, and wherein the elongated element is withdrawn from the working channel prior to the comparing.

According to a further feature of the present invention, the target location is not visible in the reference image.

According to a further feature of the present invention, the reference image and the real-time video image are displayed simultaneously to facilitate performance of the comparing features visually by a user.

According to a further feature of the present invention, the comparing includes co-processing the reference image and at least one frame from the real-time video to determine a measure of mismatch, the method further comprising generating an alarm signal if the measure of mismatch exceeds a predefined value.

According to a further feature of the present invention, the comparing includes co-processing the reference image and at least one frame from the real-time video to determine a displacement correction required to compensate for erroneous movement of the endoscope, the method further comprising generating a display indicative to a user of the displacement correction required to compensate for the erroneous movement of the endoscope.

According to a further feature of the present invention, the comparing includes co-processing the reference image and at least one frame from the real-time video to determine a transformation relating the real-time video frame to the reference image, the method further comprising generating a display corresponding to the real-time video with addition of an indication of a target location, position of the indication being derived at least in part by use of the transformation.

According to a further feature of the present invention, the endoscope is a bronchoscope.

There is also provided according to the teachings of the present invention, a system for ensuring correct alignment of an endoscope during performance of an endoscopic procedure, the system comprising: (a) an endoscope having a distal end for insertion into a body; (b) an imaging arrangement associated with the endoscope and configured to generate a real-time video image of a region beyond the distal end; and (c) a processing system associated with the imaging arrangement and configured to: (i) in an initial state of alignment with a target location, derive from the imaging arrangement a reference image corresponding to correct alignment with the target location, (ii) derive from the imaging arrangement real-time images of the region beyond the distal end, and (iii) co-process the reference image and the real-time images to determine a current alignment status of the endoscope with the target location.

According to a further feature of the present invention, the processing system is configured to co-process the reference image and the real-time images to determine a measure of mismatch, the processing system further generating an alarm signal if the measure of mismatch exceeds a predefined value.

According to a further feature of the present invention, there is also provided a display for displaying at least the real-tire images to a user, wherein the processing system is configured to co-process the reference image and the real-time images to determine a displacement correction required to compensate for erroneous movement of the endoscope, the processing system further generating an indication on the display indicative to a user of the displacement correction required to compensate for the erroneous movement of the endoscope.

According to a further feature of the present invention, there is also provided a display for displaying at least the real-time images to a user, wherein the processing system is configured to co-process the reference image and the real-time images to determine a transformation relating the real-time video frame to the reference image, the processing system further generating on the display an indication of a target location, position of the indication being derived at least in part by use of the transformation.

According to a further feature of the present invention, there is also provided a position measuring system including a position sensor carried by an elongated element removably deployable along a working channel of the endoscope.

There is also provided according to the teachings of the present invention, a method for facilitating performance of an endoscopic procedure on a target which is obscured from view by an imaging arrangement of an endoscope, the method comprising: (a) generating real-time video from the imaging arrangement of the endoscope; (b) determining a position of the target and a position of a distal end of the endoscope; (c) generating a display including the real-time video and a simulated view of the target correctly positioned within the real-time video; and (d) adjusting the display so as to maintain the target correctly positioned within the real-time video when the endoscope is moved.

According to a further feature of the present invention, the adjusting includes comparing features from at least one frame of the real-time video with features from a reference image derived from the imaging arrangement during the step of determining, thereby deriving a transformation relating the real-time video frame to the reference image.

According to a further feature of the present invention, the determining a position of a distal end of the endoscope is performed using position measuring system including a position sensor carried by an elongated element removably deployable along a working channel of the endoscope.

BRIEF DESCRIPTION OF THE DRAWINGS

The invention is herein described, by way of example only, with reference to the accompanying, drawings, wherein.

DESCRIPTION OF THE PREFERRED EMBODIMENTS

The present invention is a system and method for image-based alignment of an endoscope.

The principles and operation of systems and methods according to the present invention may be better understood with reference to the drawings and the accompanying description.

First in general terms, the present invention provides systems and methods for endoscopic procedures (exemplified herein with reference to bronchoscopic procedures) wherein a first technique is used to ensure initial correct alignment of an endoscope with a desired target and a reference image is acquired from an imaging arrangement associated with the endoscope. Then, during a subsequent stage of the procedure, tracking of the endoscope position relative to the target is performed partially or entirely by image-based tracking by comparing features in the realtime video image produced by the imaging arrangement with features in the reference image.

Thus, according to a first aspect of the present invention, a method for confirming correct alignment of a distal end of an endoscope during an endoscopic procedure includes: positioning the distal end of the endoscope adjacent to a target location and capturing, a reference image using the imaging arrangement; sensing a real-time video image using the imaging arrangement; and comparing features of the real-time video image with the reference image to confirm correct alignment of the endoscope.

It will immediately be appreciated that the present invention offers profound advantages, particularly for cases where the desired target is obscured from view (such as behind other tissue) or is not readily identifiable directly by visual imaging. In such cases, navigation under video imaging alone is insufficient. Nevertheless, after use of a primary tracking system (such as that of the aforementioned WO 03/086498) to achieve initial alignment, use of feature-based optical tracking based on features not necessarily belonging to the target frees the system from subsequent dependence on the primary tracking system, thereby allowing removal of the position measurement probe and/or rendering navigation more robust and reliable in the face of disturbances such as movement of the patient's body or the like. These and other advantages of the present invention will become clearer from the subsequent description.

Figure 10:
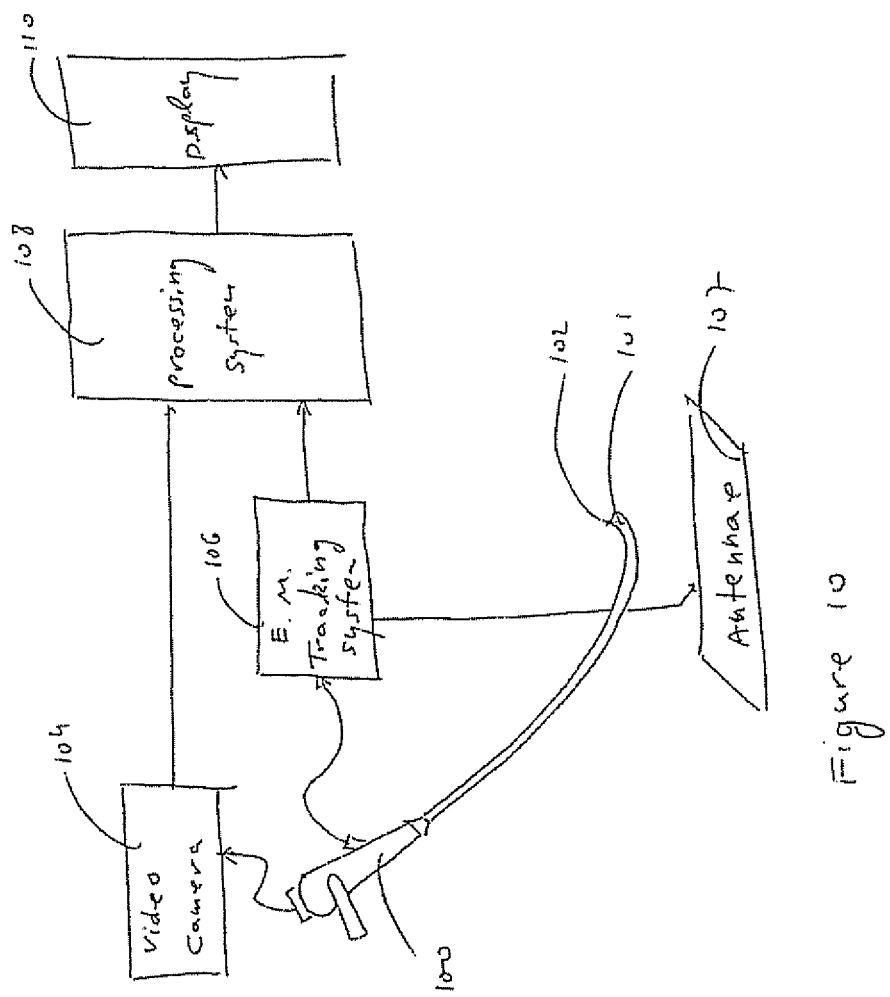
FIG. 10 is a schematic illustration of the components of a system, constructed and operative according to the teachings of the present invention, for ensuring correct alignment of an endoscope during performance of an endoscopic procedure.

Referring now to the drawings, FIG. 10 shows schematically a preferred implementation of a system, constructed and operative according to the teachings of the present invention, for implementing the methods of the present invention. For one set of preferred implementations of the method of the present invention, the system is substantially similar to that described in WO 03/086498 with certain changes to the display and/or image processing systems, as will be described below. Thus, a position measurement sensor 101 and video sensor 102 are incorporated in the distal tip of bronchoscope 100. An electro-magnetic tracking system induces electromagnetic fields from antennae 107, senses the signals from the location sensor 101 and determines the position of the tip of the bronchoscope in six degrees of freedom. A processing system 108 gathers that position information together with the video image from the tip of the bronchoscope as produced by the video camera 104. The processing system may display to the physician live video, captured images and simulated views on a display screen 110.

Further details of a particularly preferred position measuring system for measuring position in six degrees-of-freedom may be found in U.S. Pat. No. 6,188,355 and PCT Application Publication Nos. WO 00/10456 and WO 01/67035 Most preferably, at least one, and preferably three, reference sensors (not shown) are also attached to the chest of the patient and their 6 DOF coordinates sent to processing system 108 where they are used to calculate the patient coordinate frame of reference.

It should be noted in this context that the term "position sensor" is used herein in the description and claims to refer to any element which can be associated permanently or temporarily with an object and functions together with other components of a position measuring system to determine the position and/or attitude of the object. It should be appreciated that the terminology does not necessarily imply that the position sensor itself is capable of any measurement alone. Nor does this terminology imply any particular function of the position sensor, such that the "sensor" may be a transmitter, a receiver or any other element which functions as part of a position measuring system, depending upon the technology employed. In all such cases, the element is referred to as a "position sensor" since its presence associated with the object allows sensing by the system of the object's position.

Although described herein with reference to a non-limiting preferred implementation employing a bronchoscope, it should be noted that the present invention is equally applicable to substantially any intra-body endoscopic procedure.

As in the aforementioned WO 03/086498, the location of the desired target within the body is preferably determined in an offline preparation session prior to the procedure in which the target is identified in three-dimensional image data of a region of a body to be treated. The three-dimensional image data is preferably derived from an imaging technique selected from: computerized tomography; magnetic resonance imaging; positron emission tomography; and ultrasound. Most commonly, computerized tomography ("CT") data is used. Then, after suitable calibration to register the position measurement system coordinates with the CT data, a simulated tip view or other visual navigation aids as described in WO 03/086498 are used to guide the bronchoscope into alignment with the target. These navigation aids are based on comparing the position of the distal end of the endoscope as measured by the position measuring system and the target location as identified in the image data. Then, according to one particularly preferred set of embodiments, the position sensor is withdrawn from a working channel of the endoscope as part of an elongated element.

Figure 1:
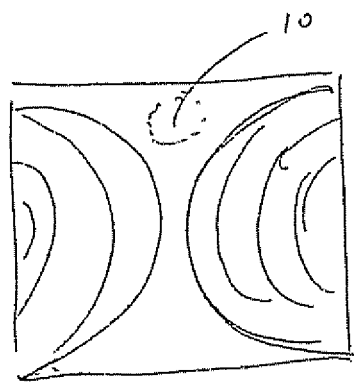
FIG. 1 is a video display of the target zone inside the bronchial tree when the tip of the bronchoscope is off target.

FIGS. 1-4 illustrate schematically examples the displays which are preferably available to the physician during initial alignment of the bronchoscope. Specifically, FIG. 1 shows an example of a target area. The target is obscured from view, being located behind the tissue of a bifurcation inside the bronchus. The target 10, marked in a broken line, is not visible in the video image. In one embodiment of the invention, it is not marked in the video display at all. In another preferred embodiment it's the target's location, as calculated by the processing system 108, is displayed in the video display by an artificial mark such as a line, a point, a broken line, a colored area, a three dimensional entity or a combination of any of the above.

Figure 2:
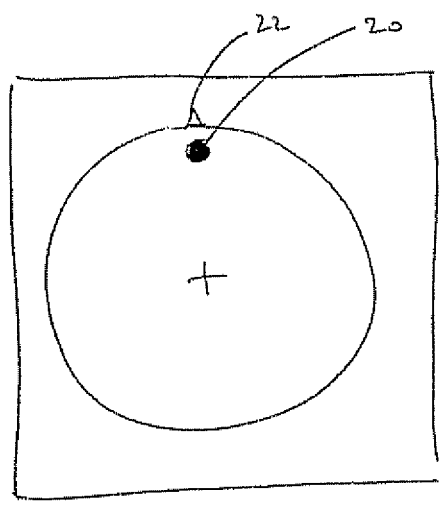
FIG. 2 is a simulated tip view corresponding to the position of FIG. 1.
Figure 3:
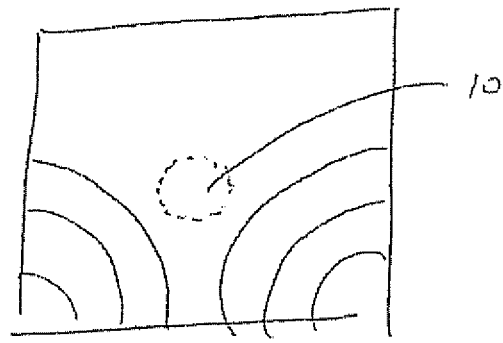
FIG. 3 is a video display of the target zone inside the bronchial tree when the tip of the bronchoscope is on the target.
Figure 4:
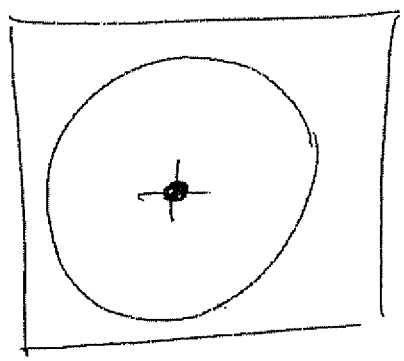
FIG. 4 is a simulated tip view corresponding to the position of FIG. 3.
Figure 5:
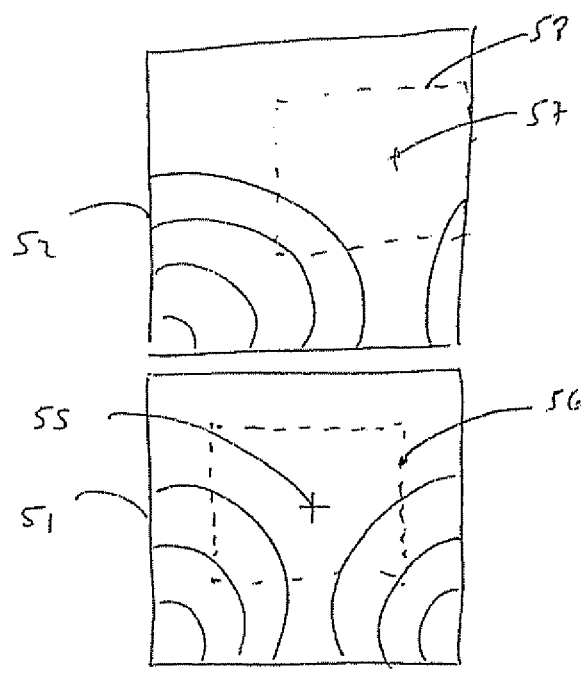
FIG. 5 is a display of a combination of a stored image and live video in the context of first preferred embodiment of the invention.

In FIG. 1, the tip of the bronchoscope is shown to be positioned off the direction of the target. FIG. 2 is the tip view used for directing to the target. The direction of the target relative to the tip is presented by dot 20 marking the target and arrow 22 aiming from the tip to the target. The target may also be presented in a simulated view of the boundary of the actual target lesion as calculated from the CT data or by a colored area or by three-dimensional entity or by any combination of the above. According to the example, the tip should be deflecting in the 12 o'clock direction in order to be on target FIGS. 3 and 4 show the same scenario when the tip is on target. According to the prior art described above, after achieving alignment with the target as shown, the physician has to try to hold the bronchoscope steady while withdrawing the locatable guide and inserting a tool along the lumen. According to the present invention, before the guide is withdrawn, the image as shown in FIG. 3 is captured and stored in a memory device of processing system 108. Now the system has two sources of images to control the location of the bronchoscope's distal tip, a real-time live video image 52 and a captured video image 51 where the tip was located at the desired target location, as shown in FIG. 5.

The present invention may be implemented in a number of different embodiments with different degrees of sophistication as to how the comparison between features of the real-time video and the reference image is performed. According, to a first basic embodiment, the reference image 51 and the real-time video image 52 are displayed simultaneously on display device 110 as illustrated in FIG. 5, thereby facilitating visual comparison of the image features by a user. In this case, the physician himself compares the two images and decides whether the bronchoscope is located in the required location, and if not, in what direction the tip of the bronchoscope should be deflected.

In more sophisticated embodiments, the system preferably co-processes the reference image and the real-time images to determine a current alignment status of the endoscope with the target location. Thus, processing system 108 is configured to: derive from the imaging arrangement of the endoscope, in an initial state of alignment with a target location, a reference image corresponding to correct alignment with the target location; derive from the imaging, arrangement real-time images of the region beyond the distal end, and co-process the reference image and the real-time images to determine a current alignment status of the endoscope with the target location.

Here too, the co-processing may be implemented at various different levels of sophistication. In a simplest case, a correlation between the reference image and the current video image may offer a measure of mismatch. The user can then empirically adjust the position of the bronchoscope tip to maximize the correlation (minimize the mismatch), thereby returning to the correct position. Application of a threshold to the measure of mismatch may be used to activate an alarm signal.

In more preferred implementations, the system tracks features or regions from the reference image in the video image to provide more specific indications to the user of the required correction for any erroneous movement of the bronchoscope off target. For small-scale lateral displacements, this may be implemented simply by correlating a central sub-window 56 of reference image 51 centered on target location 55 with a corresponding sized sliding window (i.e., at multiple different positions) in the real-time video to find the best match, thereby identifying the position of the target sub-window in the real-time video image.

At a next level of sophistication the tracking may also allow for scaling and/or rotation of the sub-window. This allows the system to maintain target tracking during rotation, as well as small-scale advancing or withdrawal, of the bronchoscope. A further level of sophistication may employ planar transformations such as affine transformations which approximate the distortions caused by viewing a surface from different viewing angles.

At the top end of the range of sophistication in the tracking algorithms are tracking techniques based on three-dimensional modeling of the viewed scene and reconstruction of the camera path. Such techniques, often referred to as "Structure from Motion", are well developed in the field of optical tracking and computer vision, and allow reconstruction of three-dimensional models from a single moving camera. Details of processing techniques for implementing structure from motion may be found in papers from the Robotics Research Group in the Department of Engineering Science, Oxford University (UK) such as "Automatic Camera Tracking" by Andrew W. Fitzgibbon et al. *Video Registration* (2003) and "Feature Based Methods for Structure and Motion Estimation" by P. H. S. Torr et al. *Vision Algorithms: Theory and Practice* (2000), both available from http://www.robots.ox-.ac.uk/.

In the present application, structure-from-motion processing can be greatly simplified by the use of model data based on CT data or the like. Thus, for example, given that the initial reference image is taken from a known position as established by the primary alignment system, a "depth" (i.e., camera-to-surface distance) associated with each pixel of the reference image can be derived directly from CT data, thereby providing an initial three-dimensional model from which processing can begin. This approach has advantages of robustness under significant changes of view, and even where there is no overlap between the current real-time video field of view and the reference image.

In any or all of the above-mentioned tracking techniques, corrections are preferably made for geometrical distortions introduced by the optics of the imaging arrangement, as is known in the art. These corrections may be performed on the source images prior to implementing the tracking techniques, or may be incorporated into the tracking calculations themselves.

The output from the system (and method) of the present invention may take a number of forms. In a simplest case mentioned above, an alarm may be sounded if a measure of mismatch between the current video and the reference image indicates that the bronchoscope has wandered off target, and the measure of mismatch (or the correlation) may be displayed to the user or indicated by an audio signal to provide feedback indicative of "getting hotter" or "getting colder" with regard to alignment with the target.

Figure 6:
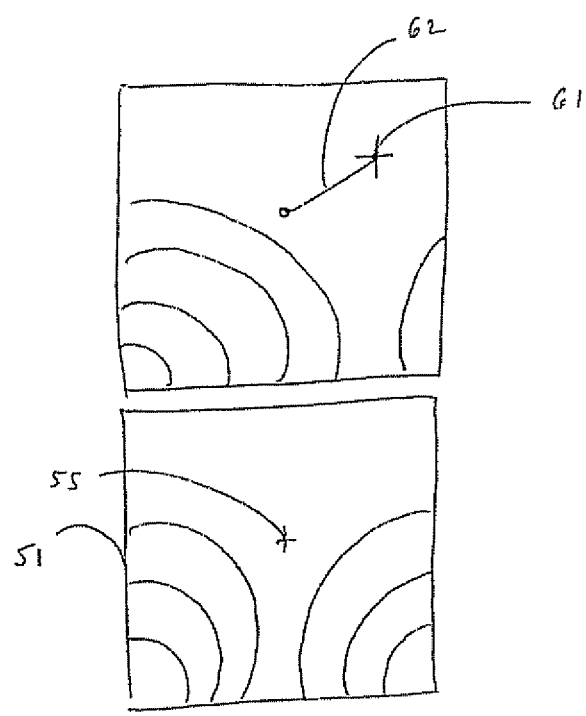
FIG. 6 is the display of a combination of a stored image and live video in the context of a second preferred embodiment of the invention.
Figure 7:
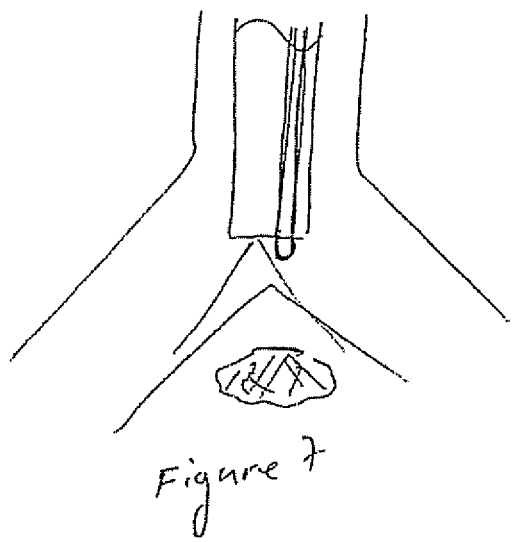
FIG. 7 is a schematic side cross-sectional view showing the bronchoscope having been correctly aligned by use of a position measurement sensor with a target which is obscured from view.
Figure 8:
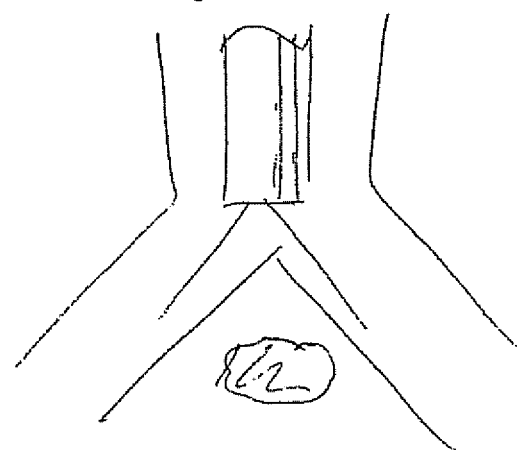
FIG. 8 is a view similar to FIG. 7 after removal of the position measurement sensor to free a working lumen of the bronchoscope.
Figure 9A:
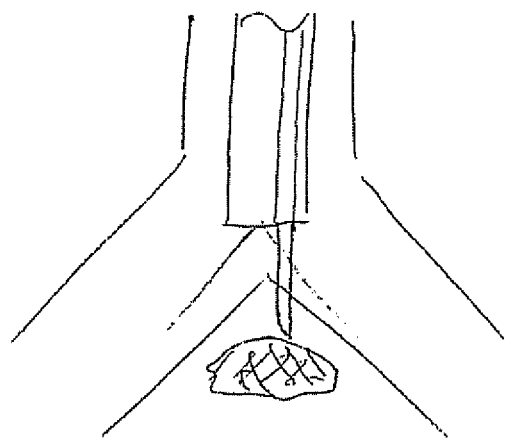
FIG. 9a is a view similar to FIG. 8 after insertion of a tool along the working lumen.
Figure 9B:
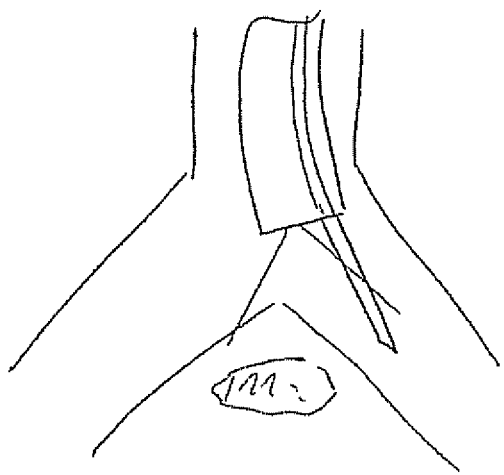
FIG. 9b is a view similar to FIG. 9a after erroneous movement has disrupted alignment of the tool with the obscured target.

In more preferred implementations where features of the reference image are positively tracked within the real-time video, the processing system may generate an indication on the display indicative to a user of the displacement correction required to compensate for the erroneous movement of the endoscope. This may take the form of all arrow or vector such as line 62 in FIG. 6 which indicates the movement of the bronchoscope required to bring the center of the field of view into alignment with the target position illustrated as 61. Thus, FIG. 6 corresponds to the display when the bronchoscope is in the position of FIG. 9b. After performing the required corrective motion, the bronchoscope returns to the position of FIG. 9a and the live video 52 of FIG. 6 would again appear similar to the reference image 51.

Alternatively, or additionally, a transformation (2 or 3 dimensional) calculated by the processing system for relating the real-time video frame to the reference image may be used to determine the position of the obscured target within the real-time video image. The target location can then be designated in the real-time video image, for example, by the sub-window frame 58 or the marker 57 as shown in FIG. 5.

According to a most preferred option, which is believed to be of patentable significance in its own right, the present invention provides an augmented reality endoscopic display in which a simulated view of an obscured target is displayed in the context of the real-time video so that the target appears correctly positioned within the video image and moves so as to maintain the correct positioning of the target within the real-time video when the endoscope is moved. This augmented reality display allows the user to operate the endoscope in a fully intuitive manner as if the target were directly viewable via the video imaging arrangement of the endoscope. Thus, the user will see obscured target 10 of FIGS. 1 and 3 as if the tissue in front of the target was semi-transparent.

In practical terms, the simulated view of the target used for the augmented reality display is preferably derived from three-dimensional imaging data such as CT in which the target tissue has been designated prior to the procedure. The target tissue volume is then preferably exported as a three-dimensional graphic object, or a closed body geometrical approximation to the tissue volume is generated. Then, during the procedure, information regarding the relative positions and orientations of the endoscope tip and the target tissue is used to determine the position, viewing angle and scaling factors which should be used to represent the target correctly in the real-time video image. The target is preferably indicated as a semi-transparent video overlay so that it appears as a ghost image without completely hiding the tissue actually viewed in the video image. Alternatively, a dashed outline or any other suitable indication may be used.

The augmented reality display is advantageous both during initial alignment of the endoscope with the target and during subsequent performance of a procedure. Most preferably, during a procedure, real-time adjustment of the simulated target image within the video image is performed on the basis of the optical tracking of the present invention. Where optical tracking is performed in two dimensions only, the adjustment of the target appearance will correspondingly be reduced to a two-dimensional manipulation. Where three-dimensional model based tracking is used, full three-dimensional augmented reality functionality is preferably maintained.

In each case, an alarm is preferably activated if the location error, i.e., the misalignment of the real-time video from the reference image, exceeds a predefined value, for example, the size of the target. The alarm may be an audio alarm and/or a visual alarm indication such as a flashing symbol or a color change of part or all of the display. An alarm (which may be distinct from the off-target alarm) is preferably also generated if the tracking algorithm fails to maintain reliable tracking between the reference image and the current image.

As mentioned earlier, the optical tracking of the present invention does not require the target location to be visible in the reference image. In fact, it should be noted that the reference image need not even include the direction to the target in its field of view. For example, if an endoscope is to be used in a procedure with a tool which generates images, takes samples or otherwise treats a region of tissue located laterally next to the distal end of the endoscope, the imaging arrangement of the endoscope will typically not offer a view of the tissue of the target, nor of any tissue which overlies the target. Nevertheless, once correct alignment of the endoscope has been achieved using the primary tracking system, the optical tracking of the present invention based on a reference image of the scene beyond the tip of the endoscope is effective to ensure correct alignment with the target, despite the fact that the target is outside the field of view.

It will be appreciated that the above descriptions are intended only to serve as examples, and that many other embodiments are possible within the scope of the present invention as defined in the appended claims.

What is claimed is:

1. A method for confirming correct alignment of a distal end of an endoscope including an imaging arrangement during an endoscopic procedure, the method comprising:
   positioning the distal end of the endoscope adjacent to a target location and capturing a reference image using the imaging arrangement;
   sensing a real-time video image using the imaging arrangement;
   comparing features of the real-time video image with the reference image to determine whether the endoscope is correctly aligned;
   if the endoscope is not correctly aligned:
      measuring a mismatch between the reference image and the real-time video image;
      providing a visual indication of the mismatch, the visual indication including directionality and magnitude information; and
      adjusting a position of the endoscope based on the directionality and magnitude information derived from the mismatch; and
   correlating a sub-window of the reference image provided on a display, and centered on the target location, with a corresponding sliding window of the real-time video image provided on the display.

2. The method of claim 1, wherein said step of positioning employs a target location identified in three-dimensional image data of a region of a body to be treated.

3. The method of claim 2, wherein said three-dimensional image data is derived from an imaging technique selected from: computerized tomography; magnetic resonance imaging; positron emission tomography; and ultrasound.

4. The method of claim 1, wherein the positioning step employs a position sensor associated with the distal end of the endoscope, said position sensor configured to aid in the measuring of the mismatch between the reference image and the real-time video image.

5. The method of claim 4, wherein the positioning step is performed by comparing a position of the distal end of the endoscope as measured in the measuring step and the target location.

6. The method of claim 4, wherein said position sensor is part of an elongated element deployed within a working channel of the endoscope, and wherein said elongated element is withdrawn from the working channel prior to said comparing step.

7. The method of claim 1, wherein said target location is not visible in said reference image.

8. The method of claim 1, further comprising displaying simultaneously said reference image and said real-time video image to facilitate the visual indication of the mismatch.

9. The method of claim 1, wherein said comparing step includes co-processing said reference image and at least one frame from the real-time video image, the method further comprising generating an alarm signal if the visual indication of the mismatch exceeds a predefined value.

10. The method of claim 1, wherein said comparing includes co-processing said reference image and at least one frame from said real-time video to determine a displacement correction required to compensate for erroneous movement of the endoscope, the method further comprising generating a display indicative to a user of said displacement correction required to compensate for the erroneous movement of the endoscope.

11. The method of claim 1, wherein said comparing includes co-processing said reference image and at least one frame from said real-time video to determine a transformation relating said real-time video frame to said reference image, the method further comprising generating a display corresponding to said real-time video with addition of an indication of a target location, position of said indication being derived at least in part by use of said transformation.

12. The method of claim 1, wherein the endoscope is a bronchoscope.

13. A system for ensuring correct alignment of an endoscope during performance of an endoscopic procedure, the system comprising:
   an endoscope having a distal end for insertion into a body;
   an imaging arrangement associated with said endoscope and configured to generate a real-time video image of a region beyond said distal end; and
   a processing system associated with said imaging arrangement and configured to:
      (i) in an initial state of alignment with a target location, derive from said imaging arrangement a reference image corresponding to correct alignment with the target location,
      (ii) derive from said imaging arrangement real-time images of the region beyond said distal end,
      (iii) co-process said reference image and said real-time images to determine a current alignment status of said endoscope with the target location,
      (iv) if said endoscope is not currently aligned:
      measure a mismatch between the reference image and the real-time video image;
      provide a visual indication of the mismatch, the visual indication including directionality and magnitude information; and
      adjust a position of the endoscope based on the directionality and magnitude information derived from the mismatch; and
      (v) correlate a sub-window of the reference image provided on a display, and centered on the target location, with a corresponding sliding window of the real-time video image provided on the display.

14. The system of claim 13, wherein said processing system is configured to co-process said reference image and said real-time images, said processing system further generating an alarm signal if the visual indication of the mismatch exceeds a predefined value.

15. The system of claim 13, further comprising a display for displaying at least said real-time images to a user, wherein said processing system is configured to co-process said reference image and said real-time images to determine a displacement correction required to compensate for erroneous movement of the endoscope, said processing system further generating an indication on said display indicative to a user of said displacement correction required to compensate for the erroneous movement of the endoscope.

16. The system of claim 13, further comprising a display for displaying at least said real-time images to a user, wherein said processing system is configured to co-process said reference image and said real-time images to determine a transformation relating said real-time video frame to said reference image, said processing system further generating on said display an indication of a target location, position of said indication being derived at least in part by use of said transformation.

17. The system of claim 13, further comprising a position sensor carried by an elongated element removably deployable along a working channel of said endoscope.

* * * * *